(12) United States Patent
Szymkowiak et al.

(10) Patent No.: US 11,300,556 B2
(45) Date of Patent: Apr. 12, 2022

(54) METHODS FOR CHARACTERISING AND MINIMISING THE CORROSIVE EFFECTS OF AN OIL

(71) Applicants: LA HARPE D'OR, Lyons (FR); EAB GROUPE, Lyons (FR); Bertrand Jean Szymkowiak, Lyons (FR); Albert Veld, Salon de Provence (FR); Franck Louis Simon Partouche, Marennes (FR); Costanza Musso, Lyons (FR)

(72) Inventors: Bertrand Jean Szymkowiak, Lyons (FR); Albert Veld, Salon de Provence (FR); Franck Louis Simon Partouche, Marennes (FR); Costanza Musso, Lyons (FR); Alain Partouche, Villeurbanne (FR); Mohamed El Younani, Montagny (FR)

(73) Assignees: LA HARPE D'OR, Lyons (FR); EAB GROUPE, Lyons (FR)

( * ) Notice: Subject to any disclaimer, the term of this patent is extended or adjusted under 35 U.S.C. 154(b) by 647 days.

(21) Appl. No.: 15/763,522

(22) PCT Filed: Sep. 28, 2015

(86) PCT No.: PCT/FR2015/052578
§ 371 (c)(1),
(2) Date: Mar. 27, 2018

(87) PCT Pub. No.: WO2017/055691
PCT Pub. Date: Apr. 6, 2017

(65) Prior Publication Data
US 2018/0313808 A1 Nov. 1, 2018

(51) Int. Cl.
*G01N 33/28* (2006.01)
*G01N 17/00* (2006.01)
*C10G 75/02* (2006.01)

(52) U.S. Cl.
CPC ....... *G01N 33/2847* (2013.01); *G01N 17/006* (2013.01); *G01N 33/2876* (2013.01);
(Continued)

(58) Field of Classification Search
CPC .. G01N 17/006; G01N 33/2847; C10G 75/00; C10G 75/02; C10G 2300/805; C10G 2300/208; C10L 1/125; C10L 10/04
See application file for complete search history.

(56) References Cited

U.S. PATENT DOCUMENTS

2012/0160709 A1  6/2012 Kusinski et al.

OTHER PUBLICATIONS

Groysman, A.; Erdman, N. "A study of corrosion of mild steel in mixtures of petroleum distillates and electrolytes," Corrosion; Dec. 2000; 56, 12; p. 1266-1271. (Year: 2000).*

(Continued)

*Primary Examiner* — Jennifer Wecker
*Assistant Examiner* — Michelle Adams
(74) *Attorney, Agent, or Firm* — Nath, Goldberg & Meyer; Joshua B. Goldberg

(57) ABSTRACT

Problems relating to metal corrosion in petroleum exploitation plants are monitored by methods, which include the following steps: i. Modifying the petroleum water content ii. Measuring the metal corrosion of metal in contact with the petroleum of step i. iii. Building, by repeating step i and step 2 several times, a database of water content values and values of metal corrosion corresponding to the respective water content values, and iv. Processing the database to determine an optimum value or an optimum range of values of water content (Mw) of the petroleum when metal corrosion shows a minimum value ($M^{CR}$).

7 Claims, 3 Drawing Sheets

(52) U.S. Cl.
CPC ....... *C10G 75/02* (2013.01); *C10G 2300/203* (2013.01); *C10G 2300/208* (2013.01); *C10G 2300/805* (2013.01)

(56) References Cited

OTHER PUBLICATIONS

International Search Report, in English and French, dated Mar. 22, 2016, for PCT/FR2015/052578, published as WO 2017/055691 A1 on Apr. 6, 2017.

\* cited by examiner

METHODS FOR CHARACTERISING AND MINIMISING THE CORROSIVE EFFECTS OF AN OIL

This is a National Phase Application filed under 35 U.S.C. 371 as a national stage of PCT/FR2015/052578, filed Sep. 28, 2015, the content of which is hereby incorporated by reference in its entirety.

TECHNICAL FIELD

The present invention relates to the general field of petroleum exploitation and in particular the field of corrosion problems met in such exploitation plants.

More particularly, the invention relates to a method of characterization of one petroleum.

The invention also relates to a method of minimization of the corrosive effects of one petroleum.

The invention also relates to a petroleum exploitation plant comprising at least one circuit formed at least in part of metal line elements within which petroleum circulates.

PRIOR ART

Petroleum exploitation requires to solve a certain number of technical problems, amongst which the corrosion of the petroleum exploitation plants by the petroleum. Indeed, petroleum, by its composition, proves to be intrinsically a corrosive medium. Moreover, this natural corrosivity is accentuated within petroleum exploitation plants by the high temperatures and flow velocities implemented. It hence results therefrom a premature degradation of the elements of such plants and particularly of the inner side of the elements in which the petroleum circulates, as for example lines, pipes, tanks, columns or other pieces of equipment, given that these latter are generally made of metal material, a material that is not expensive and easy to implement but particularly sensitive to the phenomenon of corrosion.

From then on, many problems, linked to the corrosion of such pieces of equipment may appear within a petroleum exploitation plant, such as, for example, leaks, cracks or fouling, causing in particular a lowering of the plant yield, a reduction of the flow rate, a waste of material, or even environmental and industrial risks (explosions, fire, pollution, etc.), which can sometimes cause a total failure of the plant. These problems being of course very harmful to the operators of a petroleum plant, many preventive and/or curative measures (maintenance, replacement, cleaning, etc.), on the different plant elements liable to be impaired by the petroleum corrosivity, must be taken. It results therefrom an increase of the cost of exploitation of the petroleum exploitation plants.

These problems are particularly present in the plants treating crude petroleums coming from deep petroleum reservoirs. Indeed, such "depth" petroleums are often particularly acid, and hence intrinsically very corrosive. From then on, it is easy to understand all the stakes that may exist in finding efficient and cheap solutions to reduce the corrosion problems that the petroleum plant operators are liable to meet.

Different technical trails have been explored to develop solutions making it possible to reduce the corrosion of the petroleum exploitation plants, and hence to try to overcome the above-mentioned problems.

A first solution consists in doing with the petroleum corrosivity and using, to equip the petroleum exploitation plants, materials having a high corrosion resistance, as for example stainless or highly alloyed steel. But the cost of such materials generally significantly reduces the use thereof, so that it is often inconceivable to implement them on a large scale. These materials are hence the most often reserved in practice to localized pieces of equipment of the petroleum exploitation plant.

A second alternative and/or complementary solution consists in trying to reduce the aggressiveness of the petroleum with respect to the pieces of equipment of the petroleum exploitation plant. For that purpose, it is widely known and used to inject into the petroleum different chemical substances (mainly based on phosphorus and/or sulphur), called "corrosion inhibitors". More precisely, these inhibitors, which are intrinsically corrosive components, will react to the contact with metal and then form a protective layer (iron phosphate or other) intended to protect the metal wall from the effects linked to the petroleum corrosivity . . . . This solution, only means currently available in practice to reduce the corrosion phenomena, gives relatively satisfying results from the technical point of view, by contributing to substantially reduce the corrosion problems within petroleum exploitation plants. Although it asks no particular investment at the construction of the petroleum exploitation plant, this solution proves to be, on the other hand, expensive over the long term, taking into account the cost of the chemical products implemented, and due to the fact that it is needed to permanently inject such products into the petroleum so as to modify the surfaces of the plant elements (pieces of equipment and lines, for example) to make them more resistant to corrosion. This cost problem is all the more important in the plants processing great quantities of petroleum since the quantities of inhibitors (consumables) to be daily injected are proportional to the production rate of the units.

But, in addition to the substantial financial investment over the long term, the petroleum so filled with inhibitors is liable to pose other problems to the petroleum plant operators. Indeed, the creation of a protective layer (iron phosphate or other) by action of the corrosion inhibitors requires a highly active environment, so that the whole corrosive effect is difficult to control and may often lead to undesirable and difficult to control collateral effects, as for example:
  harmful effect of the inhibitors on the catalysts of the downstream units, which degrades the efficiency of the global process,
  forming of a deposit inside the pieces of equipment, leading to the fouling of the lines, exchangers or other pieces of equipment.
  etc.

Hence, from a global or systemic point of view, although the injection of inhibitors into the petroleum potentially makes it possible to substantially reduce the corrosion of some parts of a petroleum exploitation plant (mainly the lines), other parts of the plant are on the contrary degraded due to the collateral effects of the inhibitors, these latter being accentuated by parameters such that the pressure and/or the temperature (the activity of the high-temperature corrosion inhibitors evolves with the pressure and/or the temperature).

Eventually, the implementation of active agents such as the inhibitors is paradoxically a non-negligible factor of risk for the good operation of the plant. This risk is aggravated by the fact that, in practice, a plurality of inhibitors are introduced in different and variable proportions, so that it is difficult, for the petroleum exploitation plant operation teams, to know and control the role of each of the inhibitors or chemical products injected into the petroleum, or simply to identify a parameter influencing directly the corrosion. It then generally results therefrom, to determine the different dosages, the use of empirical methods, rather inaccurate and including a non-negligible risk of error.

DISCLOSURE OF THE INVENTION

The objects assigned to the present invention hence aim to remedy the different drawbacks mentioned hereinabove and to propose a new method of characterization of one petroleum, making it possible to identify, in a simple, fast, accurate and cheap manner, a parameter of minimization of the petroleum corrosion on a metal part.

Another object of the invention aims to propose a new method of characterization of one petroleum, which is versatile and can be applied, for example, to a great variety of different petroleums, and in particular petroleums having very different total acid numbers (TAN).

Another object of the invention aims to propose a new method of characterization of one petroleum, which can be implemented in a particularly simple, safe, fast and cheap manner in a petroleum exploitation plant, including directly by the operator.

Another object of the invention aims to propose a new method of minimization of the corrosive effects of one petroleum, which does not fundamentally modify the composition of the petroleum nor the degree of acidity thereof.

Another object of the invention aims to propose a new method of minimization of the corrosive effects of one petroleum, which is particularly easy and simple to implement, while being particularly accurate.

Another object of the invention aims to propose a new method of minimization of the corrosive effects of one petroleum, which is based on an essentially analytical approach and not on a purely empirical assessment.

Another object of the invention aims to propose a new method of minimization of the corrosive effects of one petroleum, which requires no heavy investment.

Another object of the invention aims to propose a new method of minimization of the corrosive effects of one petroleum, constituting an alternative to the use of chemical corrosion inhibitors based on phosphorus or sulphur and which is particularly interesting on the economic and environmental point of view.

Another object of the invention aims to propose a new method of minimization of the corrosive effects of one petroleum, which can be implemented within a petroleum exploitation plant in a particularly simple, safe, fast and cheap manner, including directly by the operator.

Another object of the invention aims to propose a petroleum exploitation plant in which the problems of corrosion due to petroleum are minimized.

Another object of the invention aims to propose a petroleum exploitation plant that makes it possible to minimize, in a particularly simple and fast to implement manner, the problems of corrosion due to petroleum.

Another object of the invention aims to propose a petroleum exploitation plant that makes it possible to minimize, in a particularly economical manner, the problems of corrosion due to petroleum, without fundamentally impairing the composition and the properties of the petroleum and by respecting the environment.

Another object of the invention aims to propose a petroleum exploitation plant that makes it possible to minimize, in an automatable manner, the problems of corrosion due to petroleum.

Another object of the invention aims to propose a petroleum exploitation plant that makes it possible to minimize the problems of corrosion due to different petroleums, whether they come from a single crude or from different cuts.

The objects assigned to the invention are achieved by means of a method of characterization of one petroleum, wherein the petroleum is placed in contact with a metal part, and which includes the following steps:
i. Modifying the water content of the petroleum,
ii. Measuring the corrosion of said metal part by the petroleum whose water content has hence been modified,
iii. Building, by reiterating several times the two previous steps (i, ii), a database containing a plurality of different values of water content of the petroleum and a plurality of values of corrosion each corresponding to one of said values of water content,
iv. Determining, by processing said database, an optimum value or an optimum range of values of water content of the petroleum for which the corrosion of the metal part has a minimum value.

The objects assigned to the invention are also achieved by means of a method of minimization of the corrosive effects of one petroleum on a metal part, characterized in that the quantity of water in the petroleum is adjusted so that the water content is substantially equal to a value for which the corrosivity of said petroleum is minimum.

Finally, the objects assigned to the invention are also achieved by means of a petroleum exploitation plant comprising at least one circuit formed at least in part of metal line elements within which petroleum circulates, characterized in that it comprises, on the one hand, a water injection device designed to inject water into said circuit so as to modify the water content of the petroleum, in order to minimize the corrosive effects of the petroleum on said metal lines, and on the other hand, a means for determining the quantity of water to be injected.

BRIEF DESCRIPTION OF THE DRAWINGS

Other particularities and advantages of the invention will appear and be better understood from the reading of the following description, with reference to the appended drawings, given only by way of illustrative and non-limitative example, in which.

BEST WAY TO IMPLEMENT THE INVENTION

Figure 1:
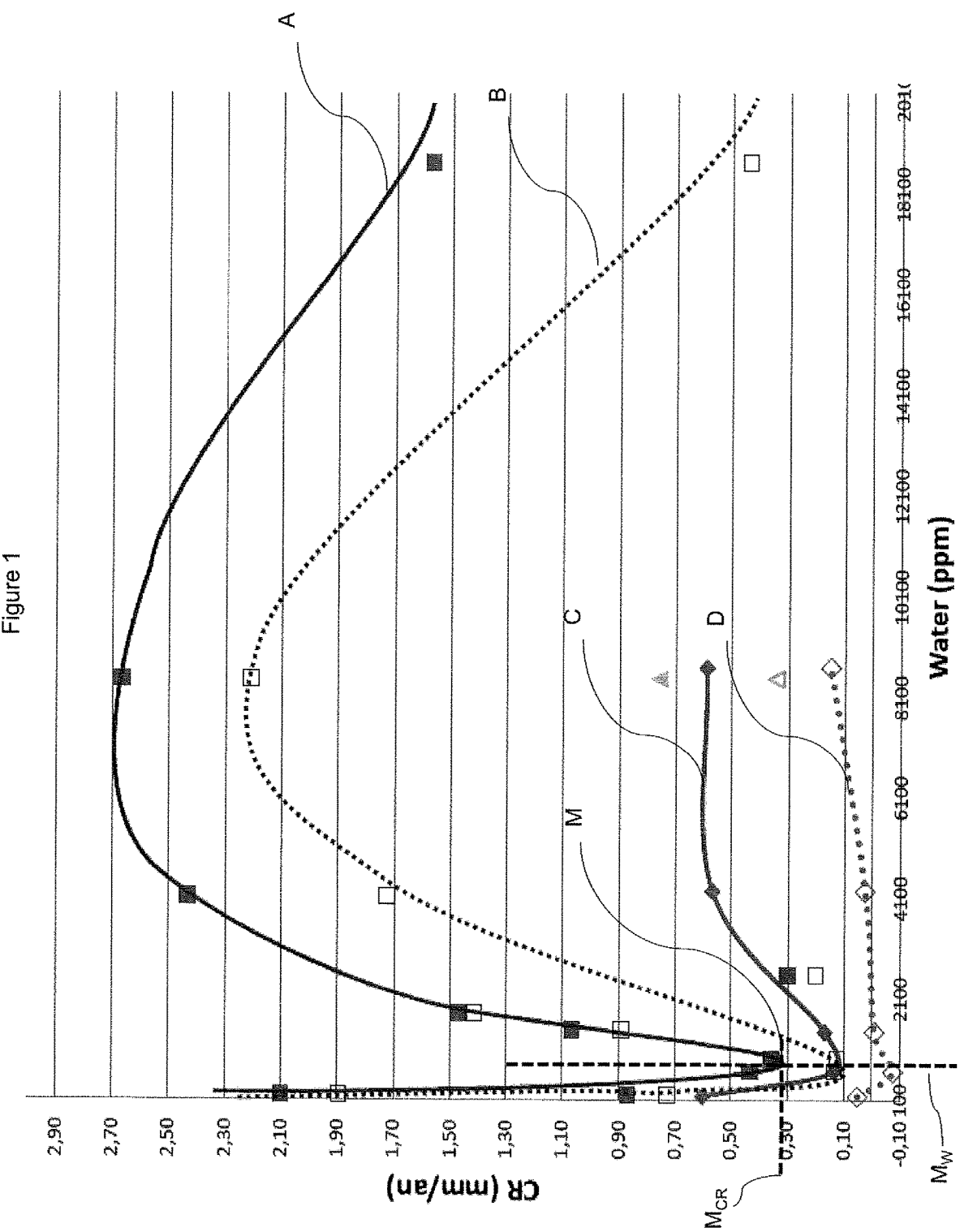
FIG. 1 shows different curves of evolution of the rate of corrosion of a metal part (in mm/year) as a function of the quantity of water in petroleum (in ppm) recorded at the time of execution of the method according to the invention applied within the framework of a first and second particular examples.

The invention relates as such to a method of characterization of one petroleum, wherein the petroleum is placed in contact with a metal part. By characterization, it is meant any operation making it possible to characterize, i.e. to show, to indicate the phenomenon that occurs. But this term can also refer to any operation that permits to understand the phenomenon that is occurring. For example, in a non-limitative way, a method of characterization generally comprises essential steps such as tests, measurements or analysis of data.

Preferentially, the method object of the invention makes it possible to characterize the level of corrosion liable to be imparted to a piece of equipment within which the petroleum in question circulates. Within the framework of the invention, the matter is preferentially the corrosion of a metal part that is in contact with one petroleum at high temperature, i.e. for example at a temperature comprised between 200 and 400° C., and preferentially of about 280° C. Indeed, by its composition, the petroleum is intrinsically a corrosive product. The term "corrosion" refers to the degradation of a part, or a material, by the action of a surrounding medium (herein petroleum), preferentially by a chemical process. The corrosion has in particular for effect the loss of material of the part or of the material in question, causing the thinning thereof and potentially going up to the perforation or even the destruction thereof.

The term "petroleum" refers both to the crude petroleum, i.e. petroleum as it comes from the petroleum reservoir during the drilling, and to the different petroleum blends or to the different petroleum cuts that come from the petroleum distillation step that is generally performed in a refinery. Likewise, this term refers to a multitude of petroleums, whichever the geographical origins, maturities, extraction depth, viscosities, densities, or total acid number (TAN) thereof. Preferentially, the term "petroleum" refers to petroleums whose total acid number, i.e. TAN, is different. The term "petroleum" may for example refer to one petroleum from West Africa, whose natural total acid number (TAN 1.5) may be artificially increased to TAN 5 (for example, by addition of naphthenic acid into the crude) for the need of said characterization.

The term "metal part" refers, without departing from the framework of the invention, to any part whose main composition is metal. Hence, the composition of this part may include any alloy and/or metal, already known or not, which includes at least one metal element, as for example steel, cast iron, stainless steel, etc. Preferentially, the term "metal part" refers a steel part, and advantageously, a carbon steel of grade ASTM A105 representative, from the metallurgical point of view, of the carbon steels frequently used in the petroleum industry. In this case, the phenomenon of corrosion of a metal part by one petroleum at high temperature (a few hundreds of degrees Celsius) is in particular due to the naphthenic acids of the petroleum that attack the carbon steel, hence forming a product of corrosion that is soluble in the organic phase, the iron naphthenate.

Similarly to its composition, the size and the shape of this part may be as varied as it can be imagined, without departing from the framework of the invention. Hence, the term "metal part" may refer both to a metal sheet of great size (a few meters) and to a plate of very small size (a few millimeters), for example to make as well a tank or a coupon, respectively. But this term may also refer to a part of more complex shape, such as a line, or a pipe, or even also an element, itself consisted of a set of parts, as for example a valve, a tap, or also a distillation column, for example within the framework of petroleum refining.

Hence, taking into account the diversity of shapes, sizes and matters that may cover the term "metal part" without departing from the framework of the invention, the term "placed in contact" may hence refer to a multitude of different situations, as long as the petroleum touches directly said metal part. Hence, as an illustrative and non-limitative way, the metal part may be in stationary contact, i.e. with no relative velocity with respect to the petroleum, as for example in the case of a tank, but may also in dynamic contact, i.e. a relative velocity exists between said metal part and the petroleum, as for example in the case of a line or a pipe within which the petroleum circulates with a certain flow velocity, as it is the case in petroleum exploitation plants, or in pipelines. Preferentially, the metal part is placed in contact with the petroleum with a relative velocity between the two materials comprised between 0 and 15 m/s and preferentially between 1 and 3 m/s.

But this contact may also refer to an "artificial" contact, i.e. a contact reproduced for the needs of an experiment, in a laboratory, whether the latter belongs to a petroleum exploitation plant or not. In this case, the part placed in contact with the petroleum will be preferentially a coupon, i.e. a metal part of a few square millimeters or centimetres and of simple shape, as for example a plate, a parallelepiped, a cylinder, a disk or a ring. Preferentially, the coupons has the shape of disks of about 15 mm in thickness and 40 mm in diameter. In this case, in order to simulate a linear flow velocity, between the petroleum and the metal part, the coupon may be placed in rotation within the petroleum and hence provide a circumferential velocity representative of a linear velocity. Preferentially, said coupon may be placed in contact with the petroleum at a circumferential velocity of the order of 6 m/s, representative of the shear stresses in operation.

The term "placed in contact" is not limited to a particular temperature and covers a great diversity of temperatures at which the metal part is in contact with the petroleum, going in particular from the ambient temperature to several hundreds of degrees Celsius. Advantageously, and as it is generally the case in the petroleum exploitation plants, the metal part is in contact with the petroleum at high temperature, i.e. for example at a temperature comprised between 200 and 400° C., and preferentially of about 280° C.

Similarly, the term "placed in contact" is not limited to a particular pressure but covers a great diversity of pressures at which the metal part is in contact with the petroleum, as for example a placement in contact under vacuum (null pressure), at the atmospheric pressure, or at a far higher pressure (several tens of bars, for example).

In the following description, reference will be made to a first particular example of implementation of the invention corresponding to the curves C and D of FIG. 1, where the interest relates to the characterization of the corrosivity of one crude petroleum of West Africa, whose natural TAN is of about 1.5. The metal part used in this example is a coupon of carbon steel of grade ASTM A105, in the form of a disk of 40 mm in diameter and 15 mm in thickness. A multitude of rigorously identical coupons is used for the good implementation of the method, as will be described hereinafter. The coupon is mounted on an axis and placed in rotation at contact with, i.e. inside, the West African petroleum, at a circumferential velocity of 6 m/s, substantially representative of a linear flow velocity of 12 m/s in a line of 4 inches. The temperature and the pressure at which this contact occurs are of 280° C. and 70 bars, respectively, and that during 24 h. Of course, this example is absolutely not limitative and the following description is transposable, without exiting from the framework of the invention, to another petroleum and/or another steel and/or other conditions, etc.

According to the invention, said characterization method includes the following steps:

i. A first step during which the water content W of the petroleum is modified. Indeed, any crude petroleum intrinsically includes a certain value of water at the time of the extraction thereof from the petroleum reservoir. The characterization method object of the invention proposes to modify this initial water content $W_i$ of the crude petroleum, either by dewatering, or by addition of water, or possibly by successive steps of dewatering then addition of water, and this, in order, in a first time, to totally remove the water from the petroleum so as to be able to very accurately control the water that is added afterwards, hence starting from a basis where the value of the water content W is substantially null. According to the first particular example of implementation of the invention described hereinabove, the water content of the West African petroleum is varied by addition of water in its liquid form into said petroleum. All the other intrinsic parameters of the petroleum (and in particular the composition, viscosity, density, maturity thereof) remain constant all over the process.

ii. A second step during which the corrosion CR of said metal part by the petroleum, whose water content W has hence been modified at the previous step is measured. Preferentially, the corrosion measurement consists in determining a loss of material of said metal part by time unit, as for example millimeters per year. This matter loss measurement may advantageously be performed by a mass loss measurement, in particular in the case where the metal part is a coupon, and/or a thickness reduction measurement, in particular in the case where the metal part has a great size. Preferentially, it is also possible to perform a pickling of the coupons (for example by means of an inhibited acid) after their placement in contact with the petroleum, and that, in order to determine the corrosion rate after exposure. Indeed, the difference between the corrosion rate before and after the coupon pickling gives information about a passive and/or protective layer formed during the exposure, as will be detailed hereinafter. According to the first particular example of implementation of the invention described hereinabove, the corrosion measurement is based on a calculation of matter loss carried out in two steps: before the coupon pickling by acid attack of the corrosion products and other different deposits of the base metal, and after coupon pickling by acid attack, as mentioned hereinabove.

iii. A third step during which is built, by reiteration several times of the two previous steps (i, ii), a database containing a plurality of different values of water content W of the petroleum and a plurality of values of corrosion CR each corresponding to one of said values of water content W, as illustrated for example by Table 1.

TABLE 1

| Measured TAN (mg KOH/g) | W Water (ppm) | CR before pickling (mm/year) | CR after pickling (mm/year) |
|---|---|---|---|
| 1.3 | 170 | 0.05 | 0.60 |
| 1.51 | 660 | −0.07 | 0.13 |

TABLE 1-continued

| Measured TAN (mg KOH/g) | W Water (ppm) | CR before pickling (mm/year) | CR after pickling (mm/year) |
|---|---|---|---|
| 1.5 | 1450 | −0.01 | 0.17 |
| 1.52 | 4240 | 0.02 | 0.57 |
| 1.51 | 8690 | 0.15 | 0.59 |

The term "database" refers to any collection in which appear different data items, and preferentially different measurements. The database visible in Table 1 has been made at the execution of the above-described first particular example of implementation of the invention. According to this example, the water content of the West African petroleum is modified, so as to obtain the five different values of water content W visible in Table 1. For each of these values, the coupon corrosion measurements are hence performed according to the above-mentioned protocol, so as to observe the values of corrosion CR before pickling and after pickling shown in the table hereinafter. Table 2 shows a similar database that is constructed according to a second particular example of implementation of the invention, whose only difference with the first example described hereinabove resides in the total acid number (TAN) of the petroleum used, which has been artificially brought to 5, as mentioned hereinabove.

TABLE 2

| Measured TAN (mg KOH/g) | W Water (ppm) | CR before pickling (mm/year) | CR after pickling (mm/year) |
|---|---|---|---|
| 4.87 | 200 | 1.90 | 2.10 |
| 4.94 | 200 | 0.73 | 0.87 |
| 4.96 | 670 | 0.13 | 0.43 |
| 5.19 | 910 | 0.12 | 0.36 |
| 4.96 | 1490 | 0.89 | 1.07 |
| 5.16 | 1800 | 1.41 | 1.47 |
| 5.21 | 2580 | 0.20 | 0.30 |
| 5.12 | 3230 | 4.75 | 5.10 |
| 5.12 | 4130 | 1.72 | 2.43 |
| 5.1 | 8470 | 2.21 | 2.67 |
| 4.98 | 18740 | 0.44 | 1.57 | iv. A fourth step during which it is determined, by processing of said database, an optimum value or an optimum range of values of water content $M_W$ of the petroleum for which the corrosion of the metal part shows a minimum value $M_{DR}$. By "processing of the database", it is referred to any intervention that consists in observing and/or processing and/or exploiting the data coming from said database. The term "optimum range of values" refers to a set of values (or one value in particular) of water content $M_W$ of the petroleum for which the corrosion of the metal part shows a minimum value $M_{CR}$. Preferentially, the optimum range of values comprises several values about an optimum value, so as to constitute a range of values, i.e. a range or a zone of values. Advantageously, the database includes enough different values of water content W of the petroleum and of corresponding values of corrosion CR so as to be able to observe, during the processing of said database, that, as the water content W of the petroleum increases, the corrosion progressively decreases then progressively increases. The term "to observe" is herein understood within the meaning of analysing, examining, the data to understand them and to be able to draw conclusions. This observation is for example advantageously realizable by means of the database visible in the first table, coming from the first particular example of implementation of the invention described hereinabove. From then on, it can be clearly seen that, as the water content W of the petroleum increases, the corrosion recorded on the metal part tends to progressively reduce before progressively increase again. More precisely, the observation of the database shows that the corrosion value seems to decrease for the values of water content of the petroleum of 170 to 1450 ppm, then seems to increase beyond these values. A similar observation may be made from the database shown in the second table, i.e. for the petroleum having the TAN substantially equal to 5: the corrosion reduces for the values of water content of the petroleum of 200 to 910 ppm, then seems to increase beyond these values.

Hence, a first observation or analysis of this database makes it already possible to characterize, according to a first approach, the level of corrosion of the petroleum on a piece of equipment as a function of a parameter: the water content thereof. It is hence already possible to determine a first approached value, by a simple processing (for example, an observation) of the database, of the optimum value of water content of the petroleum $M_W$ for which the corrosion of the metal part shows a minimum value $M_{CR}$. This approached value would be visibly comprised between 660 and 1450 ppm of water in the case of the first example of implementation of the invention, for the petroleum having a TAN of 1.5 and between 910 and 1490 ppm of water of the petroleum having a TAN of 5, in the case of the second example. Nevertheless, it is delicate to determine with accuracy the minimum value of corrosion $M_{CR}$ and the optimum value of water content $M_W$ from the experimental points presented hereinabove, so that it is preferable to continue and/or to renew the processing of the database with complementary operations described hereinafter.

Preferentially, said processing of the database comprises an operation of plotting the curve representative of the corrosion of the metal part as a function of the value of the water content of the petroleum CR=f(W). In other words, it is represented, on a diagram, the evolution of the metal part corrosion as a function of the water content of the petroleum value. The values of corrosion are placed on the ordinate axis whereas the values of water content of the petroleum are placed on the abscissa axis. Said curve includes substantially two successive segments of curve as the value of water content W of the petroleum increases:

a first segment of curve where the corrosion is a decreasing function CR=f(W) of the water content W down to a minimum point M, preferentially and substantially according to the mode of variation of the inverse function between 0 and 1, a second segment of curve where the corrosion is an increasing function CR=f(W) of the water content W from the minimum point M, preferentially and substantially according to the mode of variation of the logarithmic function.

As an alternative, in this second segment of curve, the corrosion is a substantially constant function CR=f(W) from the minimum point M.

Preferentially, said curve further includes a third segment of curve, where the corrosion tends to be stabilized according to a substantially asymptotic tendency, in particular for one petroleum having a relatively low TAN (for example TAN of 1.5).

Such an operation is for example visible in FIG. 1. More precisely, FIG. 1 includes four different curves coming from the databases shown in the previous tables, showing on the abscissa the water quantity W present in the petroleum (in parts per million) and on the ordinate the corrosion CR of the metal part (in matter loss rate, in millimeters per year).

The curve A represents the corrosion of the metal part after pickling, as a function of the water content of the West African crude petroleum, according to the second example of implementation of the invention mentioned hereinabove.

The curve B represents the corrosion of the metal part before pickling, as a function of the water content of the West African crude petroleum, according to the second example of implementation of the invention mentioned hereinabove.

The curve C represents the corrosion of the metal part after pickling, as a function of the water content of the West African crude petroleum, according to the first example of implementation of the invention mentioned hereinabove.

The curve D represents the corrosion of the metal part before pickling, as a function of the water content of the West African crude petroleum, according to the first example of implementation of the invention mentioned hereinabove.

Each of the curves, although representing different conditions, hence has substantially the same profile, i.e. the same variations, as described hereinabove.

Advantageously, said processing of the database comprises the search for the minimum point M, having for coordinates on the abscissa said optimum value $M_W$ of water content and on the ordinate said minimum value $M_{CR}$ of corrosion, for which the derivative of the corrosion as a function of the water content of the petroleum (dCR/dW) is substantially null and where it passes from a negative sign to a positive sign. In other words, if the table of variation of the function CR=f(W) is constructed, it can be observed a portion for with the derivative of said function is of negative sign (which corresponds to a decreasing function) then a portion for which the derivative is of positive sign (which corresponds to an increasing function), the two parts being separated by a value where the derivative of said function is substantially null. This value then corresponds to a minimum of said function, i.e. a value of water quantity for which the corrosion is minimum. According to the invention, this is precisely this value that is searched to be identified, characterized. Indifferently, this search for the minimum point M based on the derivative may be performed in different manners, and in particular:

by literal differentiation, knowing the function CR=f(W) and making the calculation of the derivative in a literal manner, and/or by a method of digital differentiation, i.e. by digital processing of the database, visible for example on the previous tables, et/or by a method of graphic differentiation, using the previously defined curve.

For example, the processing of the database shown in the second table, and more particularly the analysis of the curve A that follows therefrom, plotted in FIG. 1, shows that the minimum point M has for coordinates, on the abscissa, the approximate value of 1000 ppm of water and on the ordinate the approximate value of 0.31 mm/year of corrosion. In other words, in this second particular example of implementation of the invention, the water quantity $M_W$ for which the corrosivity of this petroleum is minimum $M_{CR}$ is of about 1000 ppm.

Said processing also shows, in the first and second particular examples of implementation of the invention, that this value $M_W$ is substantially common for the different curves A, B, C, D, which means that said value $M_W$ is herein independent of the total acid number (TAN) of the petroleum. It is however perfectly conceivable that, for other petroleums, the values given hereinabove are substantially or totally different, and that without departing from the framework of the invention.

According to a preferential embodiment of said method of characterization, said metal part is consisted of a metal line inside which the petroleum circulates, said line belonging to a petroleum exploitation plant, as described hereinabove (the term "petroleum exploitation plant" will be defined hereinafter). For example, the interest relates to the characterization of the corrosivity of one petroleum circulating within a petroleum exploitation plant, for example a refinery, and more precisely circulating inside a metal line. According to this embodiment, the water content W of said petroleum will be modified, then the corrosion CR of the metal line will be measured, after a certain period of time (for example, several days or weeks) that is substantial enough to record a corrosion of the line. Afterwards, the steps of modification of the water content W of the petroleum and of measurement of corrosion CR are reiterated, still with the same period of time, so as to construct a database. Then, thanks to the processing of said database, it will be possible to determine the optimum value of water content $W_C$ of the petroleum for which the corrosion of the metal line shows a minimum value $M_{CR}$.

The characterization method described hereinabove hence makes it possible to highlight, in particular thanks to the processing of the databases, that a very clear relation exists between the water content and the petroleum corrosivity, and that for different levels of total acid numbers (as it has been shown for the West African petroleum of TAN 1.5 and TAN 5 during the examples of implementation of the invention described hereinabove). In other words, the water content of one petroleum is clearly a determining factor to determine the intrinsic corrosivity of one petroleum and/or the corrosive effects thereof.

The hereinabove characterization method also makes it possible to highlight that other essential parameters come into play in the characterization of the corrosion of one petroleum. Amongst these parameters, some of them are intrinsic to the petroleum and other ones are linked to the process implemented. Hence, in addition to the water content of the petroleum, the total acid number of one petroleum represented by the value of the TAN has a predominant effect on the corrosivity thereof. As illustrated for example on the curves visible in FIG. 1, other things being equal, i.e. all the other parameters being identical (temperature, pressure, velocity, etc.), the more the TAN of one petroleum is high, the more the corrosivity thereof, i.e. the corrosion potential and hence the corrosive effects thereof will be high, and hence, the more the injection of water will have an important role to play in the method of minimization that is described hereinafter. The relative velocity between the petroleum and the metal part, in other words the flow velocity of the petroleum, is also an essential parameter in the characterization of the corrosivity of one petroleum. Indeed, the more the flow velocity is important, the more the aggressiveness of the petroleum will be high, by combination of the phenomena of erosion and corrosion.

Hence, amongst the different parameters mentioned hereinabove (TAN, temperature, pressure, velocity, water content of the petroleum, etc.) that all have a direct influence on the petroleum aggressiveness with respect to the plants, the invention has highlighted the major and unexpected role of the water content W of the petroleum, this parameter further having the advantage to be easily modifiable, without affecting the other parameters and without generating collateral effects liable to harm the exploitation.

The invention also relates, as such, to a method of minimization of the corrosive effects of one petroleum on a metal part. By "minimization method" it is meant any method by which it will be searched to substantially lower, reduce, minimize the corrosive effects and/or the corrosivity of the petroleum. The terms "corrosive", "petroleum", "metal part" are defined in the same way as hereinabove.

According to the invention, said minimization method consists in particular in adjusting the quantity of water in the petroleum so that the water content W of the petroleum is substantially equal to a value for which the corrosivity of said petroleum is minimum. The verb "to adjust" herein refers to any operation that consists in adapting, i.e. tuning, making correspond the water quantity W of the petroleum to a value close to the value for which the petroleum corrosivity is minimum. Preferentially, said quantity of water in the petroleum can be adjusted by addition of water. Furthermore, the addition of water may be completed or replaced by a removal of water, for example by means of a dewatering of the petroleum. This step may in particular make it possible, by being performed previously to the addition of water, to realize the injection of water from one petroleum that will have been totally dewatered, i.e. deprived of its initial internal water, so that the quantity of water of the petroleum will be substantially equal to the quantity of water that is added into said petroleum. Hence, it won't necessarily be required to measure the quantity of water of the petroleum, given that an accurate estimation will be directly deduced from the quantity of water added. Advantageously, the addition of water is performed in its liquid and/or gaseous form, i.e. in the form of water vapour, and preferentially from demineralized water.

Advantageously, said water content value W corresponds to the optimum value of water content $M_W$ determined by means of the characterization method described hereinabove.

Preferentially, the quantity of water in the petroleum is adjusted so that the water content of the petroleum is substantially comprised between 200 and 2000 ppm, advantageously between 500 and 1500 ppm, and preferentially of the order of 1000 ppm, these values having advantageously been determined following the implementation of the characterization method presented hereinabove, for example according to the first or second example of implementation of the invention described hereinabove, implementing West African petroleum. These values are furthermore low enough (of the order of 0.1% in mass) so as not to fundamentally modify neither the petroleum composition nor the behaviour thereof during the process, and to represent a minor, or even negligible, impact on the operational, economic plan, and a substantially null impact on the environmental plan.

Furthermore, and as can be seen on the curve A of FIG. 1, the control, i.e. the adjustment or the regulation, of the water content W of the petroleum makes it possible to reduce to substantially 90% the consumption of matter on a metal part, linked to the corrosion of the latter under the effect of the petroleum corrosivity.

According to a preferential embodiment of said minimization method, said metal part is consisted by a metal line inside which petroleum circulates, said line belonging to a petroleum exploitation plant, as previously described (the term "petroleum exploitation plant" is defined hereinafter). In other words, it comes to implement the method of minimization of the corrosive effects, in conditions similar to those described hereinabove in the previous embodiment of the characterization method, where the quantity of water will then be adjusted so as to give to the petroleum substantially a water amount value for which the corrosivity of said petroleum is minimum.

More precisely, the developed method of minimization of the petroleum corrosivity has for objective to create a protective layer on the metal part, which will then protect the latter from the attacks of the naphthenic acids of the petroleum at high temperature. This protective layer may include magnetite ($Fe_3O_4$), which may provide a protective character by itself, and/or in synergy with iron sulphur (FeS), in accordance with the following fundamental equations:

$$3Fe + 4H_2O \Leftrightarrow Fe_3O_4 + 4H_2$$

and/or $$2R\text{-}SH + 4H_2O + 4Fe \Leftrightarrow Fe_3O_4 + Fe_3 + R_2\text{-}S + 5H_2$$

Indeed, the layer of iron sulphur is the direct result of the hot attack by sulphur, whether the latter is intrinsically contained in the petroleum or, in a lesser extent, possibly added in the form of inhibitors. But, as shown by the above equations, the injection of water ($H_2O$) further allows the formation of magnetite, which has for effect to protect against the naphthenic acids of the petroleum at high temperature by itself and/or by stabilization and reinforcement of the layer of iron sulphur, hence increasing the corrosion resistance of the metal part. More precisely, the stabilizing effect of the magnetite on the layer of iron sulphur makes it possible to increase the resistance to the effect of dissolution of the iron sulphur by the naphthenic acids.

Nevertheless, the methods developed within the framework of the invention have also highlighted that this layer of magnetite is relatively difficult to obtain and/or to maintain, and that the quantity of water to be adjusted should be located in a range of values where the quantity of water is relatively low to reach a particularly low level of corrosion. Indeed, as illustrated by the previous data, and in particular the curves visible in FIG. 1, if the quantity of water becomes too high, for example beyond 2000 ppm for the West African petroleum, the corrosion rate of the metal part increases again to reach the value initially measured with the petroleum before water is injected into it, or even to exceed this level. Indeed, the methods of minimization and characterization implemented have also made possible to highlight that, beyond the optimum water content $M_W$, the water in too great quantity seems to contribute to create an acid environment, in particular by dissociation of the organic acids in the water. From then on, the development of this acid environment would tend to inhibit the action of protection of the magnetite, in particular by leading to its dissolution according to the following reaction:

$$Fe_3O_4 + 8H^+ \rightarrow 3Fe^{2+} + 4H_2O$$

As a consequence, it is crucial to correctly and accurately identify the optimum point of water content $M_W$ for which the corrosion is minimum, as described hereinabove, otherwise there exists a real risk to get again the initial corrosivity of the petroleum, or even to increase it, and hence, to aggravate the problems of corrosion of the plants.

Figure 3:
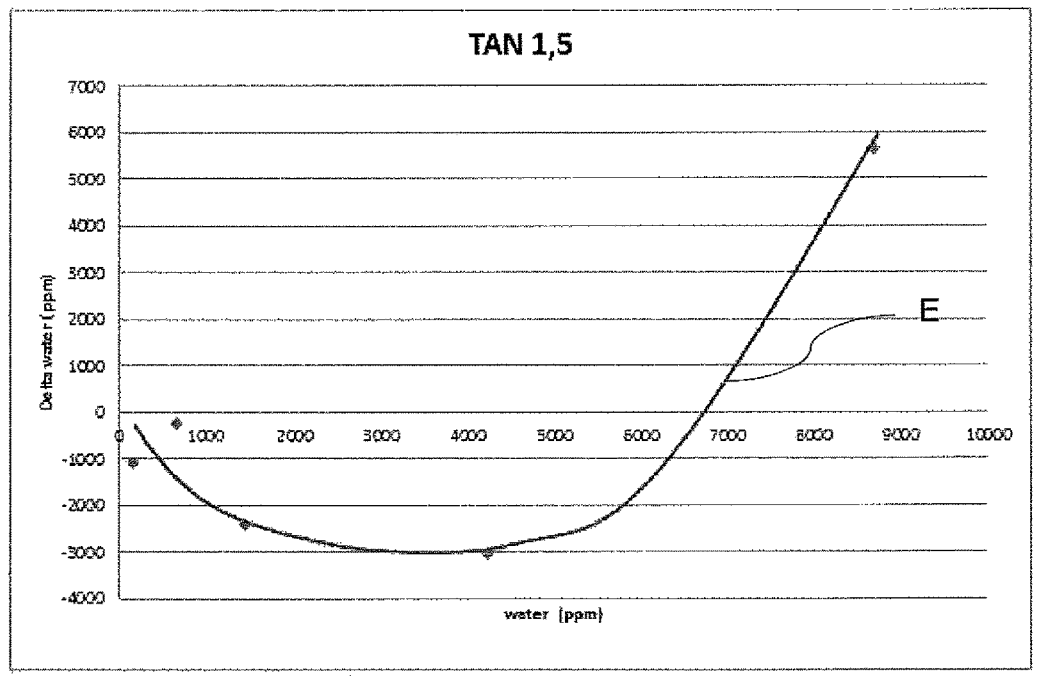
FIG. 3 shows the curve of evolution of the water content delta as a function of the initial water content recorded during a first particular example of implementation of the invention.
Figure 4:
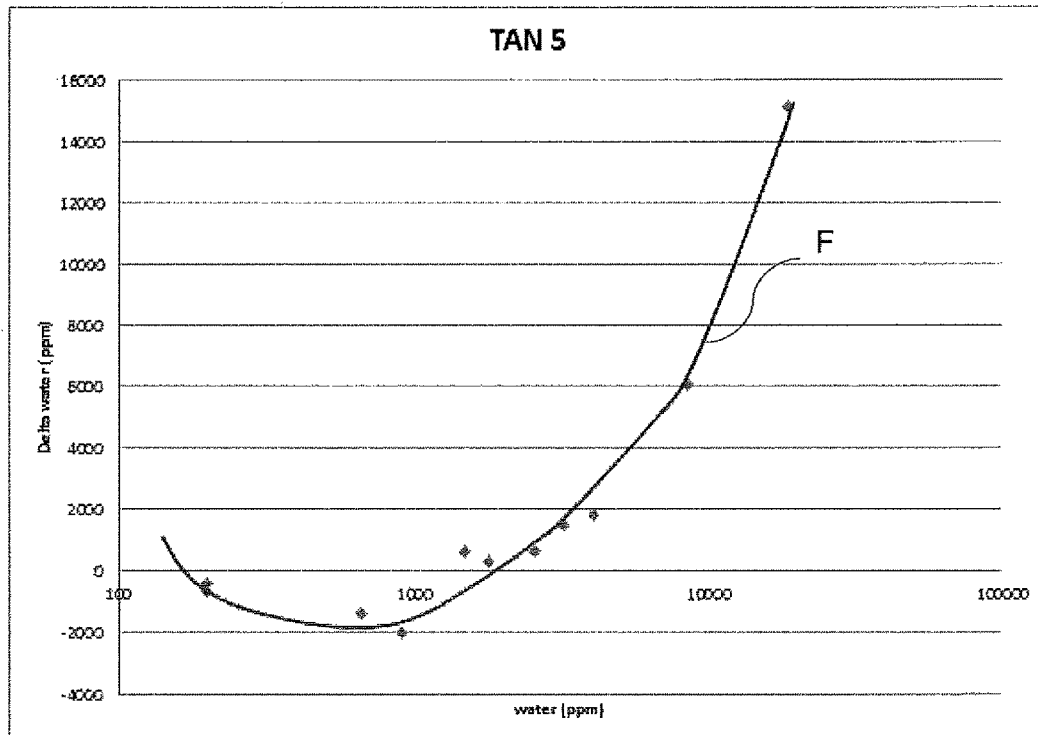
FIG. 4 shows the curve of evolution of the water content delta as a function of the initial water content recorded during a second particular example of implementation of the invention.

Another remarkable phenomenon has been highlighted during the elaboration of these methods of characterization and minimization of the corrosivity of one petroleum and directly relates to the injected water. Indeed, as illustrated by FIGS. 3 and 4, the injected water can, as a function of the total acid number (TAN) of the petroleum, be totally consummated or, on the contrary, increased, then meaning that water has been created during the method. FIG. 3 relates to the first example of implementation of the invention mentioned hereinabove and represents the curve R of evolution of the water delta (in ppm), i.e. the difference between the initial quantity of water (i.e. the quantity of water injected into the petroleum) and the final quantity of water (i.e. the quantity of water present in the petroleum once the corrosion measurement terminated) as a function of the initial quantity of water. FIG. 4 shows in a same way the curve F according to the second example of implementation of the invention mentioned hereinabove. FIG. 3 shows that, up to a certain quantity of water injected in the petroleum (approximately 7000 ppm), the final quantity of water (i.e. the quantity of water measured after the corrosion measurement after 24 h, as mentioned hereinabove) is higher than the initially injected water. In other words, water has been produced during this test. Likewise, FIG. 4 shows that water is also produced, but this time up to an initial value of water quantity of approximately 2000 ppm. This production/consumption of water has very likely a relation with the stability of the previously described protection layer that is created on the steel, even if the quantities of water created or consumed indicate that other chemical reactions, between other components present in the petroleum, come into play.

The invention also relates as such to a petroleum exploitation plant. This term refers to any plant intended for the exploitation of petroleum, going from a drilling plant, such as a petroleum platform or a drilling well, to a refining plant, such as a refinery. By extension, and without departing from the framework of the invention, any plant allowing in a more or less direct manner petroleum exploitation, is concerned by this expression, as for example a pipeline or a tank.

Figure 2:
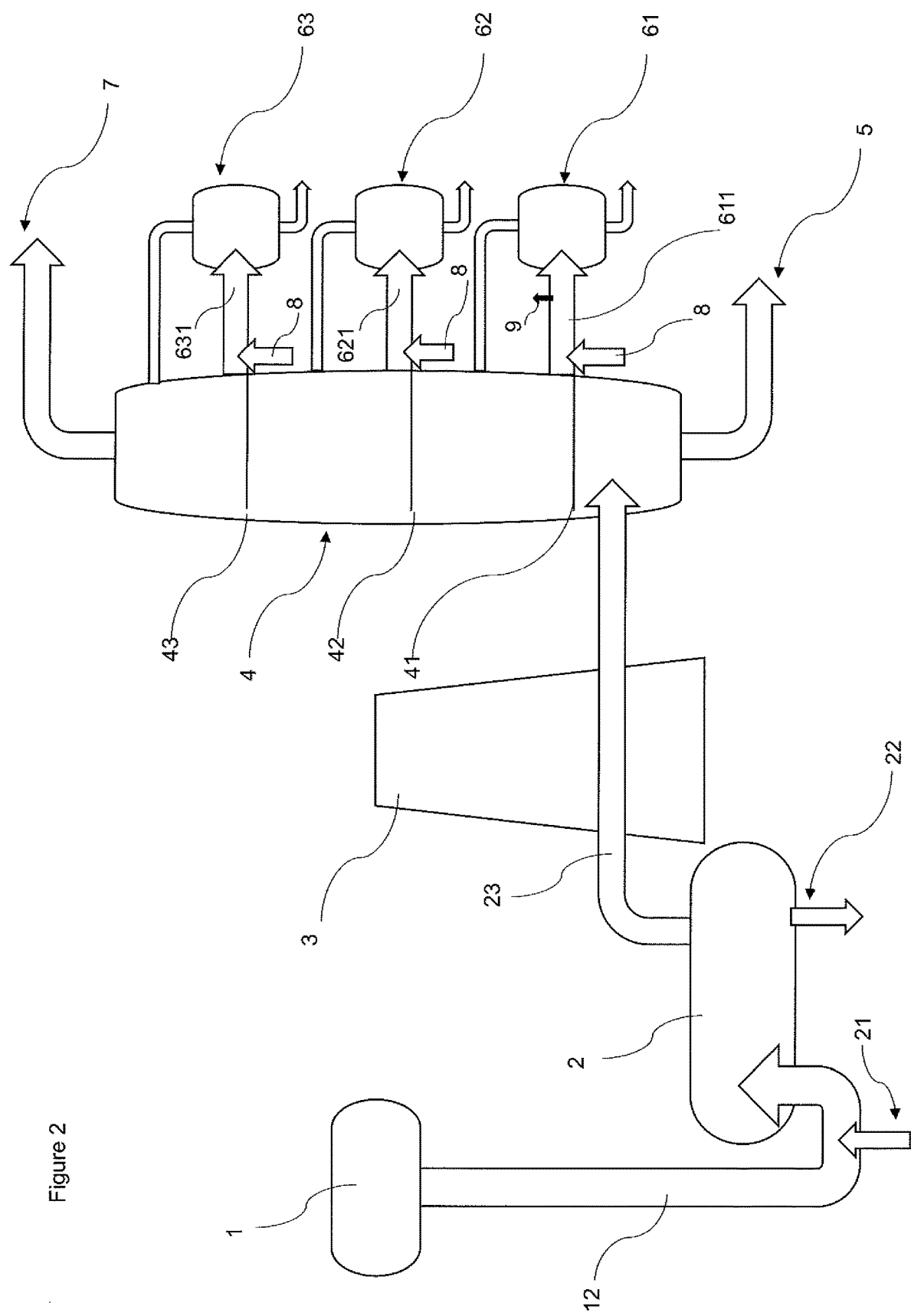
FIG. 2 schematically shows a part of a refining plant within which the corrosive effects of petroleum are minimized according to the invention.

FIG. 2 schematically and illustratively shows the principle of operation of a petroleum exploitation plant, a refinery, whose object is to transform the crude petroleum into a multitude of finished and/or semi-finished products (such as fuels, bitumens, lubricants . . . ). In a known manner, the operation of such a plant begins with a source of crude petroleum 1 that comes, for example, from a tank or directly from a pipeline. The crude petroleum is, in a first time, conveyed by means of lines 12 in a desalter 2, which includes a water intake 21 and a device for collecting water and mineral salts 22. The main function of this desalter is to extract the different mineral salts that may contain the petroleum, as for example the sodium, magnesium and calcium chlorides, so as to avoid the hydrolysis of these salts and the formation of very aggressive compounds (for example hydrogen chloride) and, in a lesser extent, that these salts are deposited, in particular under the effect of heat, in the different elements of the plant. In a known manner, this desalting function is, for example, made by injecting a great quantity (about 5%) of soft water, hence forming an emulsion, which, under the action of an electrostatic field will favour the agglomeration of the water drops containing the mineral salts, which will then be extracted after settlement 22. Once "desalted", the petroleum is then conveyed by means of lines 23 to a furnace 3 so as to heat the petroleum to a high temperature. Then the petroleum is conveyed towards the distillation column (or tower) 4. A distillation column includes different draw-off trays 41, 42, 43, and is intended to separate the molecules as a function of their molecular masses to produce different petroleum cuts. These petroleum cuts are then extracted in different draw-off circuits 611, 621, 631. By way of illustration, the circuit 61 is for example a circuit making it possible to obtain domestic fuel oil, the circuit 62, gasoil, the circuit 63, gasoline, etc. The circuit 5, located at the bottom of the column, makes it possible to obtain, for example, heavy residuals such as bitumen, whereas the circuit 7, located right at the top of the column, makes it possible to obtain gases such as butane or propane. The different draw-off circuits may include different more or less complex elements so as to produce the different finished or semi-finished products mentioned hereinabove. Of course, the elements mentioned hereinabove are given by way of illustrative and non-limitative example, and their number has been reduced in the Figure for the sake of clarity. Indeed, in practice, a distillation column includes more elements, and in particular a more important number of draw-off circuits.

According to the invention, said petroleum exploitation plant comprises at least one circuit formed at least in part of metal line elements within which petroleum circulates. By "lines", it is understood any element intended to convey the petroleum from a first point to a second point, as for example a pipe or a pipeline. By way of illustration, the line elements may be consisted by all or part of the lines 12, 23, 611, 621, 631, visible in FIG. 2. The term "metal" is understood in the same way as described above. The so-defined line elements are organized as a circuit, i.e. they form either a closed loop or an open loop so as to transport the petroleum from a starting point to an arrival point, wherein these latter can be different (in the case of an open circuit) or merged together (in the case of a closed circuit).

According to the invention, the petroleum exploitation plant comprises, on the one hand, a water injection device 8. The term "water injection device", refers to any device, means, element, member or set of elements whose main function is to inject water into another element. In other words, the water injection device 8 is able to let the water pass through from a first medium to a second medium but not reciprocally. Preferentially, said water injection device operates intermittently, i.e. it is capable of letting the water pass in one direction at certain moments, but also of being totally tight at other moments. Said device 8 may, for example, by way of illustrative and non-limitative example, be consisted by a tap or a valve equipped with a check valve, so that the water or the liquid can circulate only in one direction. Preferentially, said tap or said valve can be operated from a totally closed and tight state to a totally open state, by passing through a multitude of intermediate positions, in a continuous or on the contrary discrete manner, so as to make it possible to adjust the flow rate, i.e. to regulate the quantity of water to be injected. Advantageously, said device is able to be remote-controlled. Naturally, said water injection device is chosen amongst the known elements (valve, tap, nozzle, etc.) or made in such a manner to support the pressure and temperature stresses linked to a petroleum exploitation plant.

According to the invention, said water injection device 8 is designed to inject water into said circuit so as to modify the water content W of the petroleum that circulates in the circuit, in order to minimize the corrosive effects of the petroleum on said metal lines, as explained hereinabove.

According to the invention, the petroleum exploitation plant includes, on the other hand, a means for determining the quantity of water to be injected. By "means", it is understood any device or method that makes it possible to know the quantity of water to be injected, in other words, that makes it possible to define a target quantity of water to be reached by injection of water. Preferentially, said means to determine the quantity of water to be injected implements a method of characterization according to the previous description, so as to determine the optimum water content $M_W$ for which the corrosion CR is minimum. But, alternatively or complementarily, the means for determining the quantity of water to be injected may also be consisted of a collection of graphical charts, which, as a function of the intrinsic properties of the petroleum and/or of the conditions of use (flow velocity, temperature, line materials, etc.), would give the optimum quantity of water that the petroleum must contain to minimize the corrosion. In other words, it would be perfectly conceivable, without departing from the framework of the invention, to use, as a determination means, the existing curves visible in FIG. 1, which represent by themselves a graphical chart for the West African petroleum in the conditions of use that are described hereinabove. Advantageously, said means for determining the quantity of water to be injected is consisted by a database comprising different characteristics of the different petroleums used in the plant, so as to allow an automatic recognition of the petroleum used and an automatic determination of the quantity of water to be injected, as a function of said petroleum, to minimize the corrosive effects of the petroleum. Preferentially, said database is fed by a self-learning process which, as the exploitation of the petroleum plant goes along, records preferentially automatically the different parameters and other measured and/or calculated characteristics, linked to the different petroleums used.

Preferentially, said circuit comprises a distillation column 4 that itself includes at least one draw-off circuit 61 (as illustrated by the above-described FIG. 2), the water injection device 8 being connected to said draw-off circuit 61 so as to inject water into the latter. The term "connected" herein refers to any type of tight connection between the water injection device 8 and the draw-off circuit 61, as for example a connection made by means of an operation of cutting said circuit 61 followed by an operation of welding said water injection device 8 on the circuit. But any other assembly, as for example an assembly by means of gaskets, screws and nuts, may perfectly be implemented without departing from the framework of the invention. Preferentially, said water injection device 8 is connected to the draw-off circuit 61 by being arranged at the nearest position to the distillation column 4, and that in order to protect the whole draw-off circuit 61.

Preferentially, the water injection device 8 is designed to inject water in the form of vapour, and is hence consisted, for example, by an injection nozzle. Indeed, the injection of water in its gaseous form (vapour) allows the formation of the magnetite, hence improving the protection of the lines according to the principle detailed hereinabove. Furthermore, the vapour has the advantage to be easy to distribute and is immediately miscible, by vaporization inside the medium circulating in the previously defined circuit, i.e. inside the petroleum. Finally, great quantities of vapour are generally available in a petroleum exploitation plant, in the form of medium pressure steam (of the order of 10 to 20 bars), being hence directly usable by the water injection device 8. Advantageously, said water injection device makes it possible, using the vapour already present in the plant, to regulate the vapour from a general point of view.

Advantageously, the petroleum exploitation plant includes an evaluation device 9 for evaluating the level of corrosion CR of at least one of said line metal elements of the circuit in which the petroleum circulates. The term "evaluation device" refers to any device, i.e. any means making it possible to estimate and/or measure the corrosion. Such a device may, for example, be made by a measurement of thickness of the metal element in question, due to the fact that the corrosion is a phenomenon that reduces the thickness of the metal element. Advantageously, such a device may be made in a non-destructive and continuous manner, for example by means of a corrosion rate measurement probe, or a corrosion control device. Preferentially, such a probe is in the form of a device fixed to the line and that emits ultra-sound waves that will pass through the wall of the line. The refraction of these waves, within different materials constituting the line will then make it possible to give an indication, following operations of signal processing, in a first time of the thickness of the line, and in a second time of the rate or level of corrosion of the line. But the corrosion evaluation device may also be made by means of any other device, as, for example, a visual device (camera, endoscope, etc.) or chemical device (making it possible to detect the presence and the quantity of corrosion products) from the moment that the latter makes it possible to obtain an evaluation of the level of corrosion of at least one of the line metal elements of the circuit within which the petroleum circulates.

Preferentially, said corrosion level evaluation device 9 is connected to said draw-off circuit 61 mentioned hereinabove and visible in FIG. 2 (the term "connected" being herein defined in the same as previously), preferably after the water injection device 8, said water injection device 8 being controlled based on information coming from said evaluation device 9, through a processing means. The term "information" herein refers to any type of data, as for example digital or analog data, coming preferentially from measurements made by said device. By "processing means" it is understood any device able to determine, based on the above-described information, the way to control the water injection device, i.e. to give it the quantity of water to be injected. Such a means may be for example consisted by a computing terminal of the computer type, which is able to determine automatically the quantity of water to be injected as a function the information coming from the evaluation device 9, preferentially by implementing in an automated manner the methods of characterization and/or minimization defined hereinabove. But, alternatively or complementarily, the processing means may also be consisted of a collection of graphical charts, which, according to the level of corrosion and/or to the intrinsic properties of the petroleum and/or to the conditions of use (flow velocity, temperature, materials of the lines, etc.) would give the optimum quantity of water that the petroleum must contain to minimize the corrosion.

Advantageously, the petroleum plant includes a device for evaluating the water content W of the crude petroleum and/or of the cuts thereof and/or of the blends thereof, said water injection device 8 being controlled based on information coming from said device for evaluating the water content W of the petroleum through a processing means. In other words, instead of, or in addition to, controlling the water injection device 8 as a function of the corrosion level as defined hereinabove, it is also possible to control the latter using a means that makes it possible to provide the quantity of water contained by the petroleum. In other words, this device supposes to know beforehand, as a function of the conditions of the plant (materials, characteristics of the petroleum, temperature, velocity . . . ), the theoretical optimum quantity of water that the petroleum must contain, so as to minimize the corrosion. For example, following the previous description, it is known, that the optimum value of water content $M_W$ of the West African petroleum, to minimize the corrosivity (and/or the corrosive effects) thereof is substantially of 1000 ppm. It is hence possible, simply by means of the water content evaluation device, to control the water injection device 8, so as to reach the optimum value $M_W$. Furthermore, the presence of a device for evaluating the water content W also makes it possible to make a closed-loop control system, making it possible to maintain automatically the water content of the petroleum close to the optimum value. Hence, the previous descriptions relative to the devices, information elements and processing means also apply to this water content evaluation device.

The use of one or several of the previous evaluation devices (evaluation of the level of corrosion and/or of the water content of the petroleum) further makes it possible to automatize the injection of water into the petroleum, i.e. the plant is able, by itself, with no human intervention or with a minimum of human intervention, to adjust the quantity of water in the petroleum so as to minimize the corrosion on the different elements of said plant, and this, advantageously, substantially in real time. Hence, even if one of the previously mentioned parameters should evolve (velocity, petroleum change, temperature, pressure, etc.), the level of corrosion and/or the water content of the petroleum would evolve, the means for controlling would detect it and would then be able to automatically modify the instruction sent to the water injection device so as to modify, if need be, the water content of the petroleum.

Advantageously, the plant includes a multitude of water injection devices and of corrosion level evaluation devices 9 and/or water content of the petroleum evaluation devices, associated by pair (i.e. at least one evaluation device associated with an injection device 8) in different circuits, so that each pair of devices operates independently from each other.

Advantageously, one pair of these devices equips each of the draw-off circuits of the distillation column, which makes it possible to adjust the quantity of water to be injected in each of the circuits as a function of the proper characteristics of each of the petroleum cuts.

POSSIBILITY OF INDUSTRIAL APPLICATION

The invention finds an industrial application in particular in the implementation of a method of characterization of one petroleum and/or of a method of minimization of the corrosive effects of one petroleum in a petroleum exploitation plant, and/or in the design, making and exploitation of a petroleum exploitation plant comprising at least one circuit formed in part of metal line elements inside which petroleum circulates, as for example a petroleum platform or a refinery.

The invention claimed is:

1. A method of minimizing corrosion by a petroleum composition on a metal line in contact with the petroleum composition, the method comprising:
    circulating the petroleum composition, in at least one circuit formed at least in part from the metal line, at a temperature between 200° C. and 400° C.; and
    modifying the petroleum composition by injecting water into the circuit to adjust a water content (W) of the petroleum composition to obtain a modified petroleum composition, wherein the water content (W) of the modified petroleum composition is equal to an optimum value (Mw) between 200 and 2000 ppm.

2. The method of minimizing corrosion by a petroleum composition according to claim 1, wherein the optimum value (Mw) of water content (W) of the modified petroleum composition is between 500 and 1500 ppm.

3. The method of minimizing corrosion by a petroleum composition according to claim 1, wherein the optimum value (Mw) of water content (W) of the petroleum composition is 1000 ppm.

4. The method of minimizing corrosion by a petroleum composition according to claim 1, wherein the metal line is in a petroleum exploitation plant.

5. The method of minimizing corrosion by a petroleum composition according to claim 1, wherein the water injected into the circuit during the modifying step is in the form of vapour.

6. The method of minimizing corrosion by a petroleum composition according to claim 1, wherein the circuit comprises a distillation column that itself includes a draw-off circuit, and wherein the water injected into said circuit during the modifying step is injected into said draw-off circuit.

7. A method of minimizing corrosion by a petroleum composition on a metal line in contact with the petroleum composition, the method comprising:
    circulating the petroleum composition, in at least one circuit formed at least in part from the metal line, at a temperature between 200° C. and 400° C.; and
    prior to circulating the petroleum composition, determining an optimum value or an optimum range of values of water content (W) of the petroleum composition by the following steps:
    (i) placing a metal part in contact with a quantity of the petroleum composition, the metal part being made of a same metal as the metal line,
    (ii) modifying the water content (W) of the quantity of the petroleum composition to obtain a modified quantity of the petroleum composition,
    (iii) measuring corrosion (CR) of the metal part by the modified quantity of the petroleum composition,
    (iv) building, by reiterating several times steps (ii) and (iii), a database containing a water content (W) value for each modified quantity of the petroleum composition and a corresponding corrosion (CR) value for the metal part corresponding with each modified quantity of the petroleum composition and
    (v) determining the optimum value or the optimum range of values (Mw) of water content (W) of the petroleum composition for which the corrosion of the metal part shows a minimum value ($M_{CR}$) using the values in the database; and
    modifying the petroleum composition by injecting water into the circuit to adjust a water content (W) of the petroleum composition to obtain a modified petroleum composition, the water content (W) of the modified petroleum composition being either equal to the optimum value or within the optimum range of values ($M_w$),
    wherein values of water content (W) and corresponding values of corrosion (CR) in the database demonstrate that as the water content (W) of the petroleum increases, the corrosion progressively decreases then progressively increases.

* * * * *